(12) United States Patent
Cook

(10) Patent No.: US 6,452,019 B1
(45) Date of Patent: Sep. 17, 2002

(54) PREPARATION OF 4,5-DIAMINO-1-(2'-HYDROXYETHYL)-PYRAZOLE AND ACID ADDITION SALTS THEREOF

(75) Inventor: Phillip Michael Cook, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 10/081,299

(22) Filed: Feb. 22, 2002

(51) Int. Cl.[7] ............................................. C07D 231/38
(52) U.S. Cl. ..................................... 548/372.5
(58) Field of Search ....................... 548/372.5

(56) References Cited

U.S. PATENT DOCUMENTS

| | | |
|---|---|---|
| 2,989,537 A | 6/1961 | Druey et al. |
| 5,663,366 A | 9/1997 | Neunhoeffer et al. |
| 5,718,731 A | 2/1998 | Loewe et al. |
| 5,769,902 A | 6/1998 | Samain |
| 5,931,973 A | 8/1999 | Malle et al. |

FOREIGN PATENT DOCUMENTS

| | | |
|---|---|---|
| DE | 3432983 | 4/1985 |

*Primary Examiner*—Robert W. Ramsuer
(74) *Attorney, Agent, or Firm*—Michael J. Blake; Bernard J. Graves, Jr.

(57) ABSTRACT

Disclosed is an improved process for the preparation of 4,5-diamino-1-(2'-hydroxyethyl)pyrazole and acid addition salts thereof such as the addition salt from sulfuric acid. The process comprises a novel combination of steps beginning with an alkyl(alkoxymethylene)cyanoacetate and 2-hydroxyethylhydrazine and the formation of intermediate compounds 5-amino-4-alkoxycarbonyl-1-(2'-hydroxyethyl)pyrazole (I), 5-amino-4-carboxyl-1-(2'-hydroxyethyl)pyrazole (II), 5-amino-1-(2'-hydroxyethyl)pyrazole (III), 5-amino-1-(2'-hydroxyethyl)4-nitrosopyrazole (IV).

6 Claims, No Drawings

PREPARATION OF 4,5-DIAMINO-1-(2'-HYDROXYETHYL)-PYRAZOLE AND ACID ADDITION SALTS THEREOF

FIELD OF THE INVENTION

This invention relates to an improved process for the preparation of 4,5-diamino-1-(2'-hydroxyethyl)pyrazole and acid addition salts thereof such as the addition salt from sulfuric acid. More specifically, this invention pertains to a process for the preparation of 4,5-diamino-1-(2'-hydroxyethyl)pyrazole and acid addition salts thereof by a novel combination of steps beginning with an alkyl (alkoxymethylene)-cyanoacetate and a substituted hydrazine.

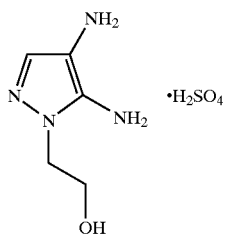

The 1-substituted-4,5-diaminopyrazoles and their addition salts are known to be especially useful as developers in combination with various couplers and an oxidizing agent for coloring keratinous fibers, particularly human hair. See, for example, U.S. Pat. Nos. 5,931,973; 5,769,902; 5,718,731; and 5,663,366.

BACKGROUND OF THE INVENTION

U.S. Pat. No. 5,663,366 discloses the preparation of 1-substituted-4,5-diamino-pyrazoles by means of a six-step process starting with pyrazole, which is difficult to handle because it is hygroscopic and an irritant. In the disclosed process, the pyrazole is first nitrated to give 4-nitropyrazole using a mixture of sulfuric and nitric acids and the 4-nitropyrazole is brominated to provide 3,5-dibromo-4-nitropyrazole. The 3,5-dibromo-4-nitropyrazole then is hydroxyethylated, using 1-bromo-2-hydroxyethane with sodium hydride in N,N-dimethylformamide as solvent, to provide 3,5-dibromo-1-(2'-hydroxy-ethyl)-4-nitropyrazole, which is then reacted with a large excess of benzylamine to provide 5-benzylamino-3-bromo-1-(2'-hydroxyethyl)-4-nitropyrazole which then is recrystallized from toluene/ligroine (1:1). Finally, the product is obtained by a complicated hydrogenation using 10 weight percent palladium-on-activated carbon (Pd/C). Under the reduction conditions, the 3-bromo group is removed, along with the benzyl group while the nitro group is reduced to amino. The product then is isolated as the sulfuric or hydrochloric acid salt. It is known that halogen atoms such as bromine and chlorine deactivate noble metal catalysts, thus posing problems in reusing the metal catalysts. This overall procedure requires the isolation of at least five products and also requires a recrystallization and the handling of very toxic reagents such as nitric acid and bromine.

German Patent DE 3432983 discloses the preparation of 4,5-diamino-1-substituted pyrazole hydrochlorides having the structure:

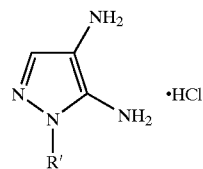

wherein R' is benzyl; benzyl substituted with halogen or hydroxy; $C_1$–$C_8$-alkyl; $C_1$–$C_4$-alkyl substituted with hydroxy. The hydrochloride compounds are not isolated but are reacted to give 1,5-disubstituted-1H-pyrazolo-(3,4-b)-pyrazines. The procedure described in DE 3432983 for the preparation of 4,5-diamino-1-substituted-pyrazole hydrochlorides utilizes a plurality of reactions and isolation of intermediate compounds.

(1) Ethyl(ethoxymethylene)cyanoacetate is reacted with a substituted hydrazine hydrochloride to provide an ethyl ester of 5-amino-1-substituted-pyrazole-4-carboxylic acid in the presence of a sodium alkoxides in methanol. The methanol is removed by distillation and replaced by acetone to allow the removal of the sodium chloride salt. The acetone from the filtrate is then removed by distillation and replaced with ethanol to facilitate the isolation of the solid product, ethyl 5-diamino-1-substituted pyrazole-4-carboxylate, which is recrystallized from ethanol.

(2) The isolated ethyl 5-diamino-1-substituted pyrazole-4-carboxylate is dissolved in methanol and hydrolyzed to the carboxyl compound by heating in the presence of 10% aqueous sodium hydroxide solution. Methanol is removed by distillation and the residue dissolved in dilute hydrochloric acid to provide the solid 5-amino-4-carboxy-1-substituted-pyrazole which is isolated by filtration, dried and then recrystallized from methanol.

(3) The isolated 5-amino-4-carboxy-1-substituted-pyrazoles is heated at 160–170° C. to effect decarboxylation to produce a 5-amino-1-substituted-pyrazole which is distilled under reduced pressure.

(4) The 5-amino-1-substituted-pyrazole was dissolved in ethanol and the resulting solution was added drop-wise to a solution of hydrogen chloride in ethanol. To the resulting solution is added drop-wise isoamyl nitrite. to nitrosate the 5-amino-1-substituted-pyrazole, producing a 5-amino-4-nitroso-1-substituted-pyrazole hydrochloride that is isolated and recrystallized.

(5) Finally, the 5-amino-4-nitroso-1-substituted-pyrazole hydrochloride is dissolved in methanol and hydrogenated in the presence of palladium-carbon catalyst. The catalyst is removed by filtration and the 4,5-diamino-1-substituted pyrazole hydrochloride is isolated by removing of the methanol or reacted directly in the methanol without isolation to provide a 1,5-disubstituted-1H-pyrazolo-(3,4-b)-pyrazine.

The process disclosed in DE 3432983 utilizes a number of isolation, recrystallization and drying operations which increase significantly the cost of preparing 4,5-diamino-1-substituted pyrazole acid salts.

Example 4 of U.S. Pat. No. 2,989,537 describes the preparation of 5-amino-4-ethoxycarbonyl-1-(2'-hydroxyethyl)-pyrazole by reacting ethyl (ethoxymethylene)-cyanoacetate with 2-hydroxyethylhydrazine in ethanol and distilling the product under vacuum at high temperature. The isolated solid product then is hydrolyzed by heating with 2N aqueous sodium hydroxide solution followed by acidification with 6N hydrochloric acid to give 5-amino-4-carboxy-1-(2'-hydroxyethyl)-pyrazole. This hydrolysis procedure in water leaves some undissolved material that must be removed by filtration. The carboxy intermediate is, heated at 160–170° C. to complete the decarboxylation and the 5-amino-1-(2'-hydroxyethyl)-pyrazole is purified by distillation under vacuum at high temperature.

In summary, the prior art procedures involve multiple isolations of intermediate products by crystallizations, recrystallizations, high temperature vacuum distillations, and other procedures and, in some cases, involve the handling and disposal of some very toxic solvents such as chlorinated hydrocarbons.

BRIEF SUMMARY OF THE INVENTION

I have developed a process comprising a plurality of process steps which provide a convenient synthesis of 4,5-diamino-1-(2'-hydroxyethyl)pyrazole and acid addition salts thereof such as the addition salt from sulfuric acid. The present invention provides an improved process for the preparation 4,5-diamino-1-(2'-hydroxyethyl)-pyrazole and acid addition salts thereof by means of the steps comprising:

(i) heating a mixture comprising an alkyl (ethoxymethylene)cyanoacetate, 2-hydroxyethylhydrazine and an alkanol to form a product solution of 5-amino-4-alkoxy-carbonyl-1-(2'-hydroxyethyl)pyrazole (I) in an alkanol;

(ii) heating the mixture of the product solution of step (i) and aqueous alkali metal hydroxide to saponify the alkoxycarbonyl ester group of (I) and remove alkanol present from the mixture and then adding sufficient acid to produce an aqueous product mixture of 5-amino-4-carboxy-1-(2'-hydroxyethyl)pyrazole (II);

(iii) separating (II) from the product mixture of step (ii) to obtain (II) as a water-wet solid;

(iv) heating water-wet (II) from step (iii) to first vaporize and remove water present and then decarboxylate (II) to produce 5-amino-1-(2'-hydroxyethyl)pyrazole (III);

(v) contacting (III) with an inorganic acid in an alkanol and contacting the resulting solution of the acid salt of (III) with a nitrosating agent to convert the acid salt of (III) to the acid salt of 5-amino-1-(2'-hydroxyethyl)-4-nitrosopyrazole (IV);

(vi) separating the acid salt of (IV) from the product mixture of step (v) to obtain the acid salt of (IV) as an alkanol-wet solid;

(vii) dissolving the alkanol-wet acid salt of (IV) from step (vi) in an alkanol to produce an alkanol solution of the acid salt of (IV) and adding a base to the solution to produce an alkanol solution of 5-amino-1-(2'-hydroxyethyl)-4-nitrosopyrazole (IV);

(viii) contacting the alkanol solution of (IV) from step (vii) with hydrogen in the presence of an insoluble hydrogenation catalyst under hydrogenation conditions of temperature and pressure to produce a product solution of 4,5-diamino-1-(2'-hydroxyethyl)pyrazole in an alkanol; and (ix) separating the insoluble hydrogenation catalyst from the product solution produced in step (viii) to obtain an alkanol solution of 4,5-diamino-1-(2'-hydroxyethyl)-pyrazole.

The process provided by the present invention eliminates many of the aforementioned intermediate isolations by high temperature; low pressure distillations, crystallizations, recrystallizations, and other costly procedures and to allow the procedure to be carried out safely and with environmentally-acceptable, recoverable solvents. Furthermore, the overall use of solvents is minimized and good overall yields of high quality 4,5-diamino-1-(2'-hydroxyethyl)pyrazole and acid addition salts thereof, particularly the sulfuric acid salt, are achieved.

The process defined above optionally may include one or both of the steps comprising:

(x) contacting the alkanol solution of 4,5-diamino-1-(2'-hydroxyethyl)pyrazole produced in step (ix) with an inorganic acid to produce an acid salt of 4,5-diamino-1-(2'-hydroxyethyl)pyrazole; and (xi) cooling the alkanol solution of the acid salt of 4,5-diamino-1-(2'-hydroxyethyl)-pyrazole produced in step (x) to cause the formation of a mixture comprising solid acid salt of 4,5-diamino-1-(2'-hydroxyethyl)pyrazole and alkanol and recovering solid acid salt of 4,5-diamino-1-(2'-hydroxyethyl)pyrazole from the mixture.

Although the process defined above may include. minor variations not specified above, the process most preferably is carried out in a manner that consists essentially of the steps set forth above.

DETAILED DESCRIPTION

In step (i) of the process, an alkanol, preferably a $C_1$–$C_3$-alkanol, solution of a 5-amino-4-alkoxycarbonyl-1-(2'-hydroxyethyl)-pyrazole (I) is prepared by reacting an alkyl (ethoxymethylene)cyanoacetate with 2-hydroxyethylhydrazine in an alkanol. The alkyl group of the alkyl(ethoxymethylene)cyanoacetate reactant and the alkoxy group of the 5-amino-4-alkoxycarbonyl-1-(2'-hydroxyethyl)-pyrazole may contain up to about 4 carbon atoms. These groups preferably are ethyl and ethoxy, respectively. Step (i) typically is carried out at a temperature in the range of about 60° C. up to the reflux or boiling temperature of the alkanol employed, preferably from about 70 up to 110° C. The alkanol solution of (I) may contain some water, e.g. up to about 30 weight percent as a result of the use of an aqueous solution of the 2-hydroxyethylhydrazine reactant.

In step (ii) of the process, the alkanol solution of (I) is contacted with an aqueous alkali metal hydroxide, preferably sodium hydroxide or potassium hydroxide, solution and heated to remove or distill off the alkanol and to saponify the alkoxy-carbonyl ester group. The conditions of temperature and pressure used in the saponification step will be sufficient to remove a vapor comprising the alkanol solvent from the saponification reaction mixture. Normally, ambient pressure and temperatures in the range of about 60° C. up to the reflux or boiling temperature of the alkanol employed, preferably from about 70 up to 110° C. depending on the particular alkanol present, are used. The amount of alkali metal hydroxide used normally is at least 1 mole per mole of (I), preferably 1 to 2 moles alkali metal hydroxide per mole of (I). The aqueous saponification reaction mixture then is contacted with an acid, e.g., an inorganic acid such as a hydrogen halide, e.g., hydrogen chloride, sulfuric acid, phosphoric acid to convert the saponified compound, i.e., an alkali carboxylate, to the carboxyl compound, i.e., 5-amino-4-carboxy-1-(2'-hydroxyethyl)-pyrazole (II). The amount of acid employed normally will provide an aqueous reaction mixture having a pH of 3 to 4, preferably about 3.75 to 4.25, most preferably about 4. The pH may be adjusted by the addition of concentrated (32–37%) hydrochloric acid or dilute (5–50%) aqueous sulfuric acid solution containing about five to about 50% by weight of sulfuric acid in water. The acidification step may be carried out at a temperature in the range of about −5 to 50° C., preferably in the range of about 0 to 25° C. In contrast to our procedures, described above, for the synthesis of compounds (I) and (II), the prior art, e.g., U.S. Pat. No. 2,989,537, Example 4, discloses the isolation and subsequent high temperature distillation of intermediate (I) under vacuum. Also, DE 3432983 discussed above provides limited information regarding the synthesis of (I) and (II). Example 1 of DE 3432983 which describes the preparation of 5-amino-1-benzyl-4-ethoxycarbonyl-pyrazole and the hydrolysis to the corresponding carboxylic acid, discloses the isolation of the intermediate ester by a complicated removal of methanol solvent, addition of acetone to render insoluble the generated ,salts, removal of the acetone by distillation and recyrstallization of the residue from ethanol. In the present invention, isolation of the intermediate ester (I) is not required and the hydrolysis is carried out in the same solvent used to complete the synthesis of the intermediate ester (I) in the presence of water and base, thus requiring only one low temperature distillation to recover the $C_1-C_3$-alkanol solvent and allowing (II) to be conveniently isolated out of water after acidification.

The separation of step (iii) may be carried out using conventional liquid/solid separation techniques such as filtration, centrifugation, and the like. Normally, the aqueous mixture from step (ii) is cooled and, optionally, agitated to effect crystallization of intermediate (II). Typically, the aqueous solution of (II) is cooled to a temperature in the range of about −5 to 10° C. and stirred to cause crystallization of (II). Compound (II) does not require drying and is used in the next step without further purification.

Step (iv) comprises heating water-wet (II) from step (iii) to remove the water present and to effect decarboxylation of (II) to convert (II) to 5-amino -1-(2'-hydroxyethyl)-pyrazole (III). Typically, the water-wet (II) is heated at a temperature of about 100 to 170°C., preferably about 135 to 155° C. The heating is continued until the evolution of carbon dioxide ceases as evidence by the cessation of foaming. Alternatively, compound (II) may be decarboxylated by heating in a high boiling solvent such as mixed xylenes using the xylenes to remove water azeotropically.

In step (v), 5-amino-1-(2'-hydroxyethyl)-pyrazole (III) produced in step (iv) is contacted with an inorganic acid in an alkanol to produce an alkanol solution of an acid salt of (III) and then contacting the alkanol solution of an acid salt of (III) with a nitrosating agent under essentially anhydrous conditions to convert the acid salt of (III) to the acid salt of 5-amino-1-(2'-hydroxyethyl)4-nitroso-pyrazole (IV). The acid used in step (v) may be selected from various inorganic acids such as a hydrogen halide, sulfuric acid and phosphoric acid. Hydrogen chloride is especially preferred. The amount of acid employed typically is at least 2 equivalents acid per mole of (III), preferably about 2 to 2.5 equivalents acid per mole of (III). The alkanol preferably is a $C_1-C_3$-alkanol, most preferably ethanol. The amount of alkanol used typically will give an alkanol:(III) weight ratio of about 4:1 to 10:1. The formation of the alkanol solution of the acid salt of (III) may be accomplished at a temperature in the range of about 20 to 60° C., preferably about 30 to 40° C. The acid addition may be carried out by dissolving (III) in an anhydrous alkanol and-then bubbling hydrogen chloride gas through the solution or an alkanol-hydrogen halide solution may be prepared separately and then added to dissolve (III). The preferred alkanol is ethanol.

The alkanol solution of the acid salt of intermediate (III) is contacted with a nitrosating agent under essentially anhydrous conditions, preferably at a temperature of less than about 25° C., preferably about −5 to 10° C., most preferably about 0 to 5° C. Examples of the nitrosating agents which may-be employed in step (vi) of the process of the present invention include nitrite esters, preferably $C_4-C_8$-alkyl nitrites, with isoamyl nitrite being particularly preferred. The amount of nitrosating agent used typically is at least 1 mole per mole of the acid salt of (III), preferably about 1 to 1.5 moles nitrosating agent per mole of the acid salt of (III).

In step (vi), the acid salt of 5-amino-1-(2'-hydroxyethyl)-4-nitroso-pyrazole (IV) is separated from the alkanol solution produced tin step (v) using conventional liquid/solid separation techniques such as filtration, centrifugation, and the like. Normally, the separation is carried out at a temperature of about −5 to 15° C. to obtain an alkanol-wet solid product. In step (vii), the alkanol-wet acid salt of (IV) is dissolved in an alkanol, e.g., a $C_1-C_3$-alkanol, and a base is added to convert the acid salt of (IV) to the free base form of (IV). The base may be selected from the carbonates, bicarbonates, and carboxylates, e.g., acetates, of the alkali and alkaline earth metals. The base preferably is potassium carbonate or sodium carbonate. The amount of base employed normally is at least 1 equivalent of base per mole of the acid salt of (IV), preferably about 1 to 1.5 equivalents of base per mole of the acid salt of (IV). This neutralization step typically is carried out at approximately ambient temperature although temperatures in the range of about 0 to 50° C. can be used. The neutralization produces an insoluble salt that normally is removed from the reaction mixture using conventional liquid/solid separation techniques such as those described above. The product of step (vii) is an alkanol solution of 5-amino-1-(2'-hydroxyethyl)-4-nitroso-pyrazole (IV).

Steps (viii) and (ix) comprise contacting the alkanol solution of (IV) from step (vii) with hydrogen in the presence of an insoluble hydrogenation catalyst under hydrogenation conditions of temperature and pressure to produce a product solution of 4,5-diamino-1-(2'-hydroxyethyl)pyrazole in an alkanol and then separating the insoluble hydrogenation catalyst from the product solution produced in step (viii) to obtain an alkanol solution of 4,5-diamino-1-(2'-hydroxyethyl)pyrazole. The hydrogenation catalyst may be selected from a variety of known noble metal hydrogenation catalysts. The hydrogenation catalyst preferably is a supported catalyst comprising a noble metal such as platinum, palladium, and the like deposited on a catalyst support material. A supported catalyst comprising about 1 to 10 weight percent palladium on carbon has been found to be an effective catalyst for the hydrogenation of step (vii). The hydrogenation conditions of temperature and pressure comprise temperatures in the range of about 0 to 50° C. and hydrogen pressures in the range of about 7 to 55 bars gauge (barg; approximately 100 to 800 pounds per square inch—psig). The preferred operating conditions comprise temperatures in the range of about 25 to 30° C. and hydrogen pressures in the range of about 34 to 41 barg (approximately 500 to 600 psig). In the procedure described in DE 3432983, Examples 8–12, intermediate (IV) is hydrogenated without neutralizing the hydrochloride salt, which results in poisoning of the noble metal catalyst which renders it inactive so that new catalyst must be provided in subsequent hydrogenation procedures. Also, when hydrochloride salt reactants are hydrogenated in conventional autoclaves constructed of nickel alloy materials the resulting product solutions have an objectionable green color. Steps (vii) and (viii) are advantageous in that they provide for the removal of troublesome hydrochloric acid and its salts to produce the free base form of (IV) which is not isolated but is converted by catalytic reduction to compound (V) which again is not isolated but optionally is converted into the final product by the addition of an acid such as sulfuric acid.

The separation of the insoluble hydrogenation catalyst may be carried out using conventional liquid/solid separation techniques such as those described above. The product solution of 4,5-diamino-1-(2'-hydroxyethyl)pyrazole in an alkanol may be used in the synthesis of other compounds or it can be contacted with an inorganic acid to produce an acid salt of 4,5-diamino-1-(2'-hydroxyethyl)pyrazole. Examples of the inorganic acids that may be used include the hydrogen halides, sulfuric acid, and phosphoric acid. The use of sulfuric acid to produce the sulfuric acid salt of 4,5-diamino-1-(2'-hydroxyethyl)pyrazole is especially preferred. This acid salt may be isolated by cooling the alkanol solution of the acid salt of 4,5-diamino-1-(2'-hydroxyethyl)pyrazole to cause the acid salt to separate as a solid material, e.g., to crystallize or precipitate, and the solid acid salt can be recovered by conventional liquid/solid separation methods.

EXAMPLE

The process provided by the present invention is further illustrated by the following example of a preferred embodiment thereof, although it will be understood that the examples are included merely for purposes of illustration and are not intended to limit the scope of the invention unless otherwise specifically indicated. All percentages given in the example are by weight unless otherwise specified.

5-Amino-4-Carboxy-1-(2'-Hydroxyethyl)-Pyrazole

Ethanol (100 mL) and 2-hydroxyethylhydrazine (75% in water) (125 g) were combined, stirred, and heated to about 70° C. Ethyl (ethoxymethylene)cyanoacetate (200 g, 1.18 mol) and ethanol (100 g) were mixed and added over about 1 hour with stirring at about 80° C. After about 2 hours the reaction was completed to give 5-amino-4-ethoxycarbonyl-1-(2'-hydroxyethyl)-pyrazole (I) as evidenced by thin-layer chromatography (ethyl acetate:methanol 7:2, silica gel). The 4-ethoxycarbonyl group was hydrolyzed to the 4-carboxylic acid group by the addition of a solution of sodium hydroxide (60 g) dissolved in water (120 g), followed by refluxing for 3 hours while ethanol was removed by distillation. The pH of the resulting solution then was adjusted at about 0–25° C. to about 4 by the addition of 32% hydrochloric acid, whereupon the tan/yellow product, 5-amino-4-carboxy-1-(2'-hydroxyethyl)pyrazole (II) began to crystallize. After being cooled and stirred at about 0–50° C. for two hours, the reaction mixture was filtered and the solid was collected for use in the next step without drying. On a dry basis, the weight yield was 145 g, 72% of the theoretical yield based on ethyl (ethoxymethylene)cyanoacetate.

5-Amino-1-(2'-Hydroxyethyl)-4-Nitrosopyrazole Hydrochloride Salt

The water-wet 5-amino-4-carboxy-1-(2'-hydroxyethyl)-pyrazole (145 g dry basis, 0.85 mol) from the procedure described above was heated to about 140° C., during which time the solid melted and water was removed by distillation. The liquid was further heated to about 150° C. while decarboxylation occurred and carbon dioxide was evolved. Foaming occurred but was controlled by stirring. After about 0.5 hour, foaming subsided and evolution of carbon dioxide ceased. The product 5-amino-1-(2'-hydroxyethyl)-pyrazole (III) was cooled to about 60° C. and 3N ethanolic HCl (700 mL) was added with stirring. Dissolution occurred upon stirring at 30–40° C. After cooling the solution, isoamyl nitrite (90 g) was added over about 40 minutes at about 0–5° C. The reaction mixture was stirred at 0–50° C. for about 2.0 hrs and the product, 5-amino-1-(2'-hydroxyethyl)-4-nitrosopyrazole hydrochloride (IV) was collected by filtration for use in the next step without drying. On a dry basis, the weight of product was 85 g, 53% of the theoretical yield based on 5-amino-1-(2'-hydroxyethyl)pyrazole.

4.5-Diamino-1-(2'-Hydroxyethyl)-Pyrazole Sulfuric Acid Salt

A portion (25 g dry basis, 0.13 mol) of the alcohol-wet 5-amino-1-(2'-hydroxyethyl)-4-nitrosopyrazole hydrochloride prepared as described above, methanol (500 mL), and potassium carbonate (25 g, 0.18 mol) were mixed and stirred for about 2 hours to neutralize the HCl. The solids were removed by filtration and the filtrate containing free base 5-amino-1-(2'-hydroxyethyl)-4-nitrosopyrazole was transferred to an autoclave and hydrogenated at 25–40° C. and 41.4 barg (600 psig) hydrogen pressure for 6 hours using a supported catalyst comprising 5% palladium on activated carbon. The mixture was cooled to 25° C. and filtered to remove the catalyst and the filtrate was cooled to about 0° C. Sulfuric acid (14 g, 93%) was added over about 30 minutes at 0–5° C. to the solution containing 4,5-diamino-1-(2'-hydroxyethyl)pyrazole. The mixture was stirred at 0–5° C. for about 3.0 hrs to complete the crystallization of the product which was collected by filtration, washed with methanol, and dried at 50° C. in a vacuum oven. The yield of the product, 4,5-diamino-1-(2'-hydroxyethyl)pyrazole sulfuric acid salt was 22 g, 71.5% of the theoretical yield based on 5-amino-1-(2'-hydroxyethyl)-4-nitrosopyrazole.

The invention has been described in detail with particular reference to preferred embodiments thereof, but it will be understood that variations and modifications can be effected within the spirit and scope of the invention.

I claim:
1. Process for the preparation of 4,5-diamino-1-(2'-hydroxyethyl)-pyrazole and acid addition salts thereof which comprises the steps of:
  (i) heating a mixture comprising an alkyl (ethoxymethylene)cyanoacetate, 2-hydroxyethylhydrazine and an alkanol to form a product solution of 5-amino-4-alkoxy-carbonyl-1-(2'-hydroxyethyl)pyrazole (I) in an alkanol;
  (ii) heating the mixture of the product solution of step (i) and aqueous alkali metal hydroxide to saponify the alkoxycarbonyl ester group of (I) and remove alkanol present from the mixture and adding sufficient acid to produce an aqueous product mixture of 5-amino-4-carboxy-1-(2'-hydroxyethyl)pyrazole (II);
  (iii) separating (II) from the product mixture of step (ii) to obtain (II) as a water-wet solid;
  (iv) heating water-wet (II) from step (iii) to remove water and to decarboxylate (II) to produce 5-amino-1-(2'-hydroxyethyl)pyrazole (III);
  (v) contacting (III) with an inorganic acid in an alkanol and contacting the resulting solution of the acid salt of (III) with a nitrosating agent under essentially anhydrous conditions to convert the acid salt of (III) to the acid salt of 5-amino-1-(2'-hydroxyethyl)-4-nitrosopyrazole (IV);
  (vi) separating the acid salt of (IV) from the product mixture of step (v) to obtain the acid salt of (IV) as an alkanol-wet solid;

(vii) dissolving the alkanol-wet acid salt of (IV) from step (vi) in an alkanol to produce an alkanol solution of the acid salt of (IV) and adding a base to the solution to produce an alkanol solution of 5-amino-1-(2'-hydroxyethyl)-4-nitrosopyrazole (V);

(viii) contacting the alkanol solution of (V) from step (vii) with hydrogen in the presence of an insoluble hydrogenation catalyst under hydrogenation conditions of temperature and pressure to produce a product solution of 4,5-diamino-1-(2'-hydroxyethyl)pyrazole in an alkanol; and (ix) separating the insoluble hydrogenation catalyst from the product solution produced in step (viii) to obtain an alkanol solution of 4,5-diamino-1-(2'-hydroxyethyl)-pyrazole.

2. Process according to claim 1 which includes the step of (x) contacting the alkanol solution of 4,5-diamino-1-(2'-hydroxyethyl)pyrazole produced in step (ix) with an inorganic acid to produce an acid salt of 4,5-diamino-1-(2'-hydroxyethyl)pyrazole.

3. Process according to claim 1 which includes the steps of:

(x) contacting the alkanol solution of 4,5-diamino-1-(2'-hydroxyethyl)pyrazole produced in step (ix) with an inorganic acid to produce an acid salt of 4,5-diamino-1-(2'-hydroxyethyl)pyrazole; and (xi) cooling the alkanol solution of the acid salt of 4,5-diamino-1-(2'-hydroxyethyl)-pyrazole produced in step (x) to cause the formation of a mixture comprising solid acid salt of 4,5-diamino-1-(2'-hydroxyethyl) pyrazole and alkanol and recovering solid acid salt of 4,5-diamino-1-(2'-hydroxyethyl)pyrazole from the mixture.

4. Process according to claim 1 wherein:

step (i) comprises heating a mixture comprising a $C_1$–$C_4$ alkyl(ethoxymethylene)-cyanoacetate, 2-hydroxyethylhydrazine and a $C_1$–$C_3$ alkanol at a temperature of about 60° C. up to the boiling point of the alkanol to form a product solution of 5-amino-4-$C_1$–$C_4$ alkoxycarbonyl-1-(2'-hydroxyethyl)pyrazole (I) in a $C_1$–$C_3$ alkanol;

step (ii) comprises heating the mixture of the product solution of step (i) and aqueous sodium or potassium hydroxide at a temperature of about 60° C. up to the boiling point of the alkanol to saponify the alkoxycarbonyl ester group of (I) and remove alkanol present from the mixture and then adding sufficient hydrochloric or sulfuric acid to produce an aqueous product mixture of 5-amino-4-carboxy-1-(2'-hydroxyethyl)-pyrazole (II);

step (iv) comprises heating at 100 to 170° C. water-wet (II) from step (iii) to remove water and to decarboxylate (II) to produce 5-amino-1-(2'-hydroxyethyl) pyrazole (III);

step (v) comprises contacting (III) with an hydrogen chloride in a $C_1$–$C_3$ alkanol at a temperature of about 20 to 60° C. and contacting the resulting solution of the acid salt of (III) with a nitrosating agent selected from $C_4$–$C_8$ alkyl nitrites at a temperature of about –5 to 10° C. under essentially anhydrous conditions to convert the acid salt of (III) to the hydrogen chloride salt of 5-amino-1-(2'-hydroxyethyl)-4-nitrosopyrazole (IV);

step (vii) comprises dissolving the $C_1$–$C_3$ alkanol-wet acid salt of (IV) from step (vi) in a $C_1$–$C_3$ alkanol to produce an $C_1$–$C_3$ alkanol solution of the acid salt of (IV) and adding a base selected from the carbonates, bicarbonates and carboxylates of the alkali metals to the solution to produce a $C_1$–$C_3$ alkanol solution of 5-amino-1-(2'-hydroxy-ethyl)-4-nitrosopyrazole (V); and step (viii) comprises contacting the $C_1$–$C_3$ alkanol solution of (V) from step (vii) with hydrogen at a temperature of about 0 to 50° C. and hydrogen pressures of about 7 to 55 bars gauge in the presence of a supported catalyst comprising a noble metal deposited on a catalyst support material to produce a product solution of 4,5-diamino-1-(2'-hydroxyethyl)pyrazole in a $C_1$–$C_3$ alkanol.

5. Process according to claim 4 which includes the step of (x) contacting the $C_1$–$C_3$ alkanol solution of 4,5-diamino-1-(2'-hydroxyethyl)pyrazole produced in step (ix) with sulfuric acid to produce the sulfuric acid salt of 4,5-diamino-1-(2'-hydroxyethyl)pyrazole.

6. Process for the preparation of the sulfuric acid salt of 4,5-diamino-1-(2'-hydroxyethyl)-pyrazole which comprises the steps of:

(i) heating a mixture comprising ethyl(ethoxymethylene) cyanoacetate, 2-hydroxy-ethylhydrazine and ethanol at a temperature of about 60° C. up to reflux temperature to form a product solution of 5-amino-4-ethoxycarbonyl-1-(2'-hydroxyethyl)pyrazole (I) in ethanol;

(ii) heating the mixture of the product solution of step (i) and aqueous sodium hydroxide at a temperature of about 60° C. up to reflux temperature to saponify the ethoxycarbonyl ester group of (I) and remove ethanol present from the mixture and then adding sufficient hydrochloric acid to confer a pH of 3.75 to 4.25 upon the reaction mixture and to produce an aqueous product mixture of 5-amino-4-carboxy-1-(2'-hydroxyethyl) pyrazole (II);

(iii) separating (II) from the product mixture of step (ii) to obtain (II) as a water-wet solid;

(iv) heating water-wet (II) from step (iii) at a temperature of about 135 to 155° C. to remove water and to decarboxylate (II) to produce 5-amino-1-(2'-hydroxyethyl)pyrazole (III);

(v) contacting (III) with hydrogen chloride in ethanol at a temperature of about 40 to 60° C. to make the acid salt of (III) and contacting the resulting solution of the acid salt of (III) with isoamyl nitrite at a temperature of about 0 to 5° C. under essentially anhydrous conditions to convert the hydrogen chloride acid salt of (III) to the hydrogen chloride acid salt of 5-amino-1-(2'-hydroxyethyl)-4-nitrosopyrazole (IV);

(vi) separating the hydrogen chloride acid salt of (IV) from the product mixture of step (v) to obtain the hydrogen chloride acid salt of (IV) as an ethanol-wet solid;

(vii) dissolving the ethanol-wet acid hydrogen chloride salt of (IV) from step (vi) in methanol to produce a methanol solution of the hydrogen chloride acid salt of (IV) and adding potassium carbonate to the solution to produce a methanol solution of 5-amino-1-(2'-hydroxyethyl)-4-nitrosopyrazole (V);

(viii) contacting the methanol solution of (V) from step (vii) with hydrogen at a temperature of about 25 to 30° C. and hydrogen pressures of about 34 to 41 bars gauge in the presence of a supported catalyst comprising palladium deposited on carbon to produce a product solution of 4,5-diamino-1-(2'-hydroxyethyl)pyrazole in methanol;

(ix) separating the supported catalyst from the product solution produced in step (viii) to obtain a methanol solution of 4,5-diamino-1-(2'-hydroxyethyl)pyrazole; and (x) contacting the methanol solution of 4,5-diamino-1-(2'-hydroxyethyl)pyrazole from step (ix) with sulfuric acid to produce the sulfuric acid salt of 4,5-diamino-1-(2'-hydroxyethyl)pyrazole.

* * * * *